(12) United States Patent
Pacetti

(10) Patent No.: US 8,846,839 B2
(45) Date of Patent: *Sep. 30, 2014

(54) COPOLYMERS HAVING ZWITTERIONIC MOIETIES AND DIHDROXYPHENYL MOIETIES AND MEDICAL DEVICES COATED WITH THE COPOLYMERS

(75) Inventor: Stephen Pacetti, San Jose, CA (US)

(73) Assignee: Abbott Laboratories, Abbott Park, IL (US)

(*) Notice: Subject to any disclaimer, the term of this patent is extended or adjusted under 35 U.S.C. 154(b) by 45 days.

This patent is subject to a terminal disclaimer.

(21) Appl. No.: 13/403,777

(22) Filed: Feb. 23, 2012

(65) Prior Publication Data
US 2012/0157602 A1 Jun. 21, 2012

Related U.S. Application Data

(60) Continuation of application No. 13/045,452, filed on Mar. 10, 2011, now Pat. No. 8,202,956, which is a division of application No. 11/942,695, filed on Nov. 19, 2007, now Pat. No. 7,928,176.

(60) Provisional application No. 60/866,800, filed on Nov. 21, 2006, provisional application No. 60/866,802, filed on Nov. 21, 2006, provisional application No. 60/866,804, filed on Nov. 21, 2006, provisional application No. 60/866,805, filed on Nov. 21, 2006, provisional application No. 60/866,798, filed on Nov. 21, 2006, provisional application No. 60/866,797, filed on Nov. 21, 2006, provisional application No. 60/866,796, filed on Nov. 21, 2006, provisional application No. 60/866,792, filed on Nov. 21, 2006.

(51) Int. Cl.
| | |
|---|---|
| C08F 30/02 | (2006.01) |
| A61L 29/16 | (2006.01) |
| A61L 31/10 | (2006.01) |
| A61L 27/34 | (2006.01) |
| A61L 27/54 | (2006.01) |
| A61L 29/08 | (2006.01) |
| A61L 31/16 | (2006.01) |

(52) U.S. Cl.
CPC .............. *A61L 27/54* (2013.01); *A61L 29/16* (2013.01); *A61L 31/10* (2013.01); *A61L 27/34* (2013.01); *A61L 2300/00* (2013.01); *A61L 29/085* (2013.01); *A61L 31/16* (2013.01)
USPC .......... 526/277; 526/312; 526/320; 526/328.5

(58) Field of Classification Search
USPC ................................ 526/277, 312, 320, 328.5
See application file for complete search history.

(56) References Cited

U.S. PATENT DOCUMENTS

| | | | |
|---|---|---|---|
| 4,141,874 | A | 2/1979 | Oka et al. |
| 4,172,934 | A | 10/1979 | Heilmann |

(Continued)

FOREIGN PATENT DOCUMENTS

| | | |
|---|---|---|
| FR | 2 863 617 | 6/2005 |
| JP | 08-059950 | 3/1996 |

(Continued)

OTHER PUBLICATIONS

U.S. Appl. No. 10/376,348, filed Feb. 23, 2003, Ding et al.

(Continued)

*Primary Examiner* — Peter D Mulcahy
(74) *Attorney, Agent, or Firm* — Squire Patton Boggs (US) LLP

(57) ABSTRACT

Copolymers are manufactured to include a zwitterionic monomer (e.g., methacryloyloxyethyl phosphorylcholine monomer), a dihydroxyphenyl derivatized monomer, and optionally one or more additional monomers. The dihydroxyphenyl derivatized monomer gives the copolymers excellent adhesion properties. Optional monomers include a cationic amino monomer, a hydrocarbon monomer, and/or a hydrophilic monomer. The copolymers are biocompatible and can be used with medical devices.

22 Claims, 1 Drawing Sheet

(56) References Cited

U.S. PATENT DOCUMENTS

| | | |
|---|---|---|
| 4,668,506 A | 5/1987 | Bawa |
| 4,931,287 A | 6/1990 | Bae et al. |
| 5,019,096 A | 5/1991 | Fox, Jr. et al. |
| 5,155,252 A | 10/1992 | Yamamoto et al. |
| 5,163,952 A | 11/1992 | Froix |
| 5,258,020 A | 11/1993 | Froix |
| 5,607,467 A | 3/1997 | Froix |
| 5,616,338 A | 4/1997 | Fox, Jr. et al. |
| 5,674,242 A | 10/1997 | Phan et al. |
| 5,723,219 A | 3/1998 | Kolluri et al. |
| 5,780,559 A | 7/1998 | Humbert et al. |
| 5,824,049 A | 10/1998 | Ragheb et al. |
| 5,859,174 A | 1/1999 | Barancyk et al. |
| 5,873,904 A | 2/1999 | Ragheb et al. |
| 5,879,713 A | 3/1999 | Roth et al. |
| 5,932,299 A | 8/1999 | Katoot |
| 5,962,138 A | 10/1999 | Kolluri et al. |
| 5,997,517 A | 12/1999 | Whitbourne |
| 6,096,070 A | 8/2000 | Ragheb et al. |
| 6,110,483 A | 8/2000 | Whitbourne et al. |
| 6,133,391 A | 10/2000 | Nielson et al. |
| 6,143,354 A | 11/2000 | Koulik et al. |
| 6,159,978 A | 12/2000 | Myers et al. |
| 6,165,338 A | 12/2000 | December et al. |
| 6,180,632 B1 | 1/2001 | Myers et al. |
| 6,214,901 B1 | 4/2001 | Chudzik et al. |
| 6,245,760 B1 | 6/2001 | He et al. |
| 6,248,129 B1 | 6/2001 | Froix |
| 6,258,371 B1 | 7/2001 | Koulik et al. |
| 6,262,034 B1 | 7/2001 | Mathiowitz et al. |
| 6,270,788 B1 | 8/2001 | Koulik et al. |
| 6,277,449 B1 | 8/2001 | Kolluri et al. |
| 6,287,707 B1 | 9/2001 | Luthra et al. |
| 6,299,604 B1 | 10/2001 | Ragheb et al. |
| 6,306,176 B1 | 10/2001 | Whitbourne |
| 6,344,035 B1 | 2/2002 | Chudzik et al. |
| 6,383,196 B1 | 5/2002 | Leslie et al. |
| 6,387,379 B1 | 5/2002 | Goldberg et al. |
| 6,419,711 B1 | 7/2002 | Genet et al. |
| 6,475,779 B2 | 11/2002 | Mathiowitz et al. |
| 6,482,834 B2 | 11/2002 | Spada et al. |
| 6,524,347 B1 | 2/2003 | Myers et al. |
| 6,528,526 B1 | 3/2003 | Myers et al. |
| 6,530,950 B1 | 3/2003 | Alvarado et al. |
| 6,530,951 B1 | 3/2003 | Bates et al. |
| 6,613,432 B2 | 9/2003 | Zamora et al. |
| 6,620,647 B2 | 9/2003 | Kroner |
| 6,663,662 B2 | 12/2003 | Pacetti et al. |
| 6,730,064 B2 | 5/2004 | Ragheb et al. |
| 6,776,796 B2 | 8/2004 | Llanos et al. |
| 6,780,930 B2 | 8/2004 | Lewis et al. |
| 6,790,228 B2 | 9/2004 | Hossainy et al. |
| 6,890,583 B2 | 5/2005 | Chudzik et al. |
| 7,005,137 B1 | 2/2006 | Hossainy et al. |
| 7,008,667 B2 | 3/2006 | Chudzik et al. |
| 7,077,859 B2 | 7/2006 | Sirhan et al. |
| 7,094,256 B1 | 8/2006 | Shah et al. |
| 7,217,426 B1 | 5/2007 | Hossainy |
| 7,247,313 B2 | 7/2007 | Roorda et al. |
| 7,396,539 B1 | 7/2008 | Hossainy et al. |
| 7,485,141 B2 | 2/2009 | Majercak et al. |
| 7,560,492 B1 | 7/2009 | Claude et al. |
| 7,563,454 B1 | 7/2009 | Pacetti |
| 7,618,937 B2 | 11/2009 | Messersmith et al. |
| 7,622,533 B2 | 11/2009 | Lee |
| 7,622,537 B2 | 11/2009 | Pacetti |
| 7,713,541 B1 | 5/2010 | Pacetti et al. |
| 7,781,551 B2 | 8/2010 | Pacetti et al. |
| 7,910,678 B2 | 3/2011 | Pacetti |
| 7,928,176 B2 | 4/2011 | Pacetti |
| 7,928,177 B2 | 4/2011 | Pacetti |
| 8,063,151 B2 | 11/2011 | Pacetti |
| 8,101,156 B2 | 1/2012 | Pacetti |
| 2001/0007083 A1 | 7/2001 | Roorda |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0051730 A1 | 5/2002 | Bodnar et al. |
| 2002/0082679 A1 | 6/2002 | Sirhan et al. |
| 2002/0111590 A1 | 8/2002 | Davila et al. |
| 2002/0133183 A1 | 9/2002 | Lentz et al. |
| 2002/0165608 A1 | 11/2002 | Llanos et al. |
| 2002/0176849 A1 | 11/2002 | Slepian |
| 2002/0188037 A1 | 12/2002 | Chudzik et al. |
| 2003/0004141 A1 | 1/2003 | Brown |
| 2003/0028243 A1 | 2/2003 | Bates et al. |
| 2003/0036794 A1 | 2/2003 | Ragheb et al. |
| 2003/0039689 A1 | 2/2003 | Chen et al. |
| 2003/0040790 A1 | 2/2003 | Furst |
| 2003/0060877 A1 | 3/2003 | Falotico et al. |
| 2003/0065377 A1 | 4/2003 | Davila et al. |
| 2003/0083739 A1 | 5/2003 | Cafferata |
| 2005/0220880 A1 | 10/2005 | Lewis et al. |
| 2006/0216326 A1 | 9/2006 | Pacetti |
| 2007/0010623 A1 | 1/2007 | Ha |
| 2008/0118541 A1 | 5/2008 | Pacetti |
| 2008/0124450 A1 | 5/2008 | Pacetti |
| 2008/0125514 A1 | 5/2008 | Pacetti |
| 2008/0125560 A1 | 5/2008 | Pacetti |
| 2008/0139746 A1 | 6/2008 | Pacetti |
| 2008/0146696 A1 | 6/2008 | Pacetti |
| 2008/0147178 A1 | 6/2008 | Pacetti et al. |
| 2008/0153923 A1 | 6/2008 | Pacetti |
| 2008/0220046 A1 | 9/2008 | Cheng et al. |

FOREIGN PATENT DOCUMENTS

| | | |
|---|---|---|
| WO | WO 98/22517 | 5/1998 |
| WO | WO 99/08729 | 2/1999 |
| WO | WO 2006/102418 | 9/2006 |

OTHER PUBLICATIONS

"Block Copolymers Containing Bioadhesive end Groups", Biomacromolecules 3, pp. 397-406 (2002).

Dyneon™ Fluorothermoplastics—Product Information (2000).

Huang et al., "Synthesis and characterization of Self-Assembling Block Copolymers Containing Bioadhesive end Groups", Biomacromolecules 3, pp. 397-406 (2002).

Hull et al. THV Fluoroplastic in Modern Fluoropolymers ed. J Scheirs 1997 p. 257.

Kocakulak et al., "Investigation of Blood Compatibility of PMEA Coated Extracorporeal Circuits", J. of Bioactive and Compatible Polymers vol. 17, pp. 343-356 (2002).

Lee et al.,"Synthesis and Gelation of DOPA-Modified Poly(ethylene glycol) I lydrogels", Biomacromolecules 3, pp. 1038-1047 (2002).

Maccone et al. Macromoelcules 33: pp. 1656-1663 (2000).

Sipos et al. Biomacromolecules 6: pp. 2570-2582 (2005).

Solvay, SolexisTecnoflon® P757 product information, 10 pgs. (2003).

Tanaka et al., "Blood compatible aspects of poly(2-methoxyethylacrylate) (PMEA)-relationship between protein adsorption and platelet adhesion on PMEA surface", Biomaterials 21, pp. 1471-1481 (2000).

Tecnoflon® p. 757 (2003).

Trollsas et al., "Hyperbranched Poly(ε-caprolactone) Derived from Interinsically Branched AB2 Macromonomers", Macromolecules 31, pp. 4390-4395 (1998).

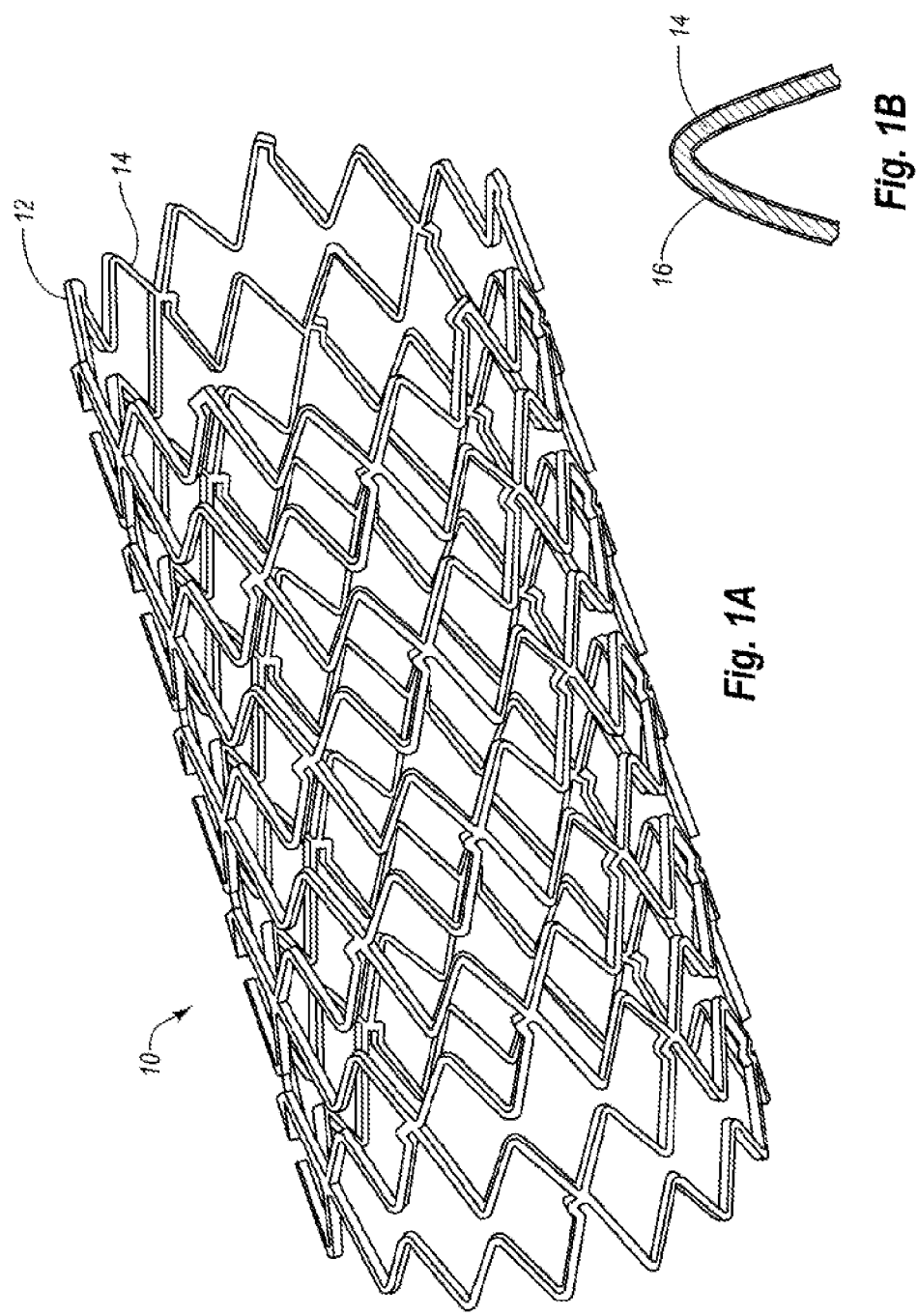

COPOLYMERS HAVING ZWITTERIONIC MOIETIES AND DIHDROXYPHENYL MOIETIES AND MEDICAL DEVICES COATED WITH THE COPOLYMERS

CROSS-REFERENCE TO RELATED APPLICATIONS

This application is a continuation application of U.S. application Ser. No. 13/045,452 filed on Mar. 10, 2011, which is a divisional application of U.S. application Ser. No. 11/942,695 filed on Nov. 19, 2007, the teaching of which is incorporated by reference herein in its entirety. U.S. application Ser. No. 11/942,695 claims the benefit of U.S. Provisional Patent Applications Nos. 60/866,800, 60/866,802, 60/866,804, 60/866,805 60/866,798, 60/866,797, 60/866,796, 60/866,792, all of which were filed on Nov. 21, 2006, and all of which are hereby incorporated by reference in their entirety. U.S. application Ser. No. 11/942,695 is related to co-pending U.S. patent application Ser. No. 11/942,704, entitled "Methods of Manufacturing Copolymers with Zwitterionic Moieties and Dihydroxyphenyl Moieties and Use of Same", co-pending U.S. patent application Ser. No. 11/942,693, entitled "Zwitterionic Copolymers, Method of Making and Use on Medical Devices", co-pending U.S. patent application Ser. No. 11/942,705, entitled "Amino Acid Mimetic Copolymers and Medical Devices Coated with the Copolymers", co-pending U.S. patent application Ser. No. 11/942,696, entitled "Methods for Manufacturing Amino Acid Mimetic Copolymers and Use of Same", co-pending U.S. patent application Ser. No. 11/942,700, entitled "Copolymers Having 1-Methyl-2-Methoxyethyl Moieties", and co-pending U.S. patent application Ser. No. 11/942,707, entitled "Methods for Manufacturing Copolymers having 1-Methyl-2-Methoxyethyl Moieties and Use of Same", all of which were filed on Nov. 19, 2007, and all of which are hereby incorporated by reference in their entirety. Co-pending U.S. patent application Ser. No. 11/939,512 filed Nov. 13, 2007 and co-pending application Ser. No. 11/562,338 filed Nov. 21, 2006 are hereby incorporated by reference in their entirety.

BACKGROUND OF THE INVENTION

1. The Field of the Invention

Embodiments of the invention relate to biocompatible copolymers and medical devices coated with the copolymers. More particularly, embodiments of the invention relate to copolymers having zwitterionic monomers and monomers with dihydroxyphenyl moieties.

2. The Related Technology

Implantable medical devices, including stents, can be coated with polymers to give the implantable device beneficial properties when used in living tissue. Implant coatings, particularly stent coatings, typically need to simultaneously fulfill many criteria. Examples of desirable properties for implant coating properties include: adhesion to the implant (e.g., adhesion to stent struts) to prevent delamination; adequate elongation to accommodate implant deformation without buckling or cracking; sufficient hardness to withstand crimping operations without excessive damage; sterilizability; ability to control the release rate of a drug; biocompatibility including hemocompatibility and chronic vascular tissue compatibility; in the case of durable or permanent coatings, the polymer needs to be sufficiently biostable to avoid biocompatibility concerns; processability (e.g., production of stent coatings that are microns thick); reproducible and feasible polymer synthesis; and an adequately defined regulatory path.

Recently, polymers containing 2-(methacryloyloxyethyl)-2'-(trimethylammoniumethyl) phosphate("phosphorylcholine or "PC") monomers have been developed and used on implant devices. PC containing polymers have been shown to have many beneficial properties. For example, PC containing polymers are typically sterilizable, biocompatible, made from commercially available reagents, have received regulatory approval for certain embodiments, and provide a controlled drug release rate for higher molecular weight drugs.

However, PC coatings still need improvements with regard to adhesion. Specifically, PC containing polymers have relatively poor adhesion to many implantable medical devices. The lack of good adhesion can necessitate the use of a primer to improve bonding, which can complicate the manufacture and use of the implantable device.

SUMMARY OF THE INVENTION

The embodiments of the invention relate to copolymers with zwitterion moieties and implantable medical devices coated with the zwitterionic copolymers. In addition to the zwitterion moiety, the co-polymers of embodiments of the invention include a dihydroxyphenyl moiety that provides improved adhesion to the surface of a medical device.

The copolymers of embodiments of the invention can be manufactured by copolymerizing a zwitterionic monomer with a dihydroxyphenyl monomer to yield a thermoplastic polymer. The copolymers can optionally include a cationic amino monomer, a hydrocarbon monomer, and/or a hydrophilic monomer.

In one embodiment, the copolymers of embodiments of the invention have the following formula,

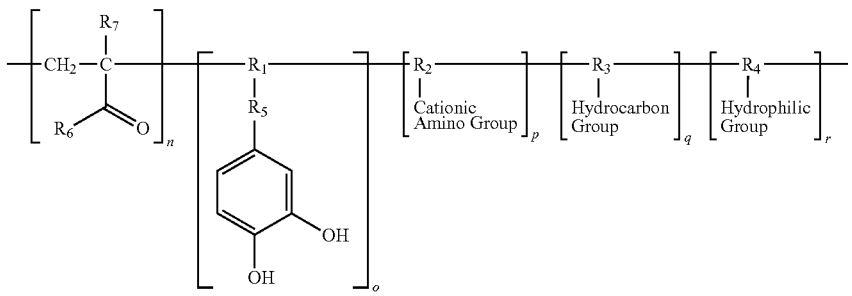

In the foregoing formula, $R_1$-$R_4$ are independently a methacryl, acryl, styryl, acrylamido, methacrylamido, sulfovinyl, amido, ester, ethyl, or propyl; $R_5$ is a hydrocarbon chain, cycloaliphatic group, ester group, amide group, thiol, sulfone, carbonate, saccharide, PEG, or combination thereof; $R_6$ includes a zwitterion group, a linker being a chain of 2-12 carbon atoms, and an ester or amide attachment to the methacryl group; $R_7$ is a methyl, ethyl, or hydrogen group; n is in a range from about 0.005 to about 0.5; o is in a range from about 0.005 to 0.4; p is optionally included in a range from 0.005 to 0.25; q is in a range from 0.005 to 0.98; and r is optionally included in a range from 0.005 to 0.4. In one example embodiment, n+o+p+q+r=1.

These and other advantages and features of the invention will become more fully apparent from the following description and appended claims, or may be learned by the practice of the invention as set forth hereinafter.

BRIEF DESCRIPTION OF THE DRAWINGS

To further clarify the above and other advantages and features of the invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings, in which:

FIG. 1A illustrates an example of a stent coated with a zwitterionic copolymer according to one embodiment of the invention; and FIG. 1B is a cross-section of a strut of the stent of FIG. 1A.

DETAILED DESCRIPTION OF EMBODIMENTS OF THE INVENTION

I. Copolymers

Embodiments of the invention relate to copolymers for use as a coating on implantable medical devices. The copolymers include a zwitterionic monomer (e.g., methacryloyloxyethyl phosphorylcholine monomer), an ortho-dihydroxyphenyl derivatized monomer, and one or more additional, optional monomers.

For purposes of this invention, the term acrylate monomer includes monomers that are methacrylates or acrylates.

1. Zwitterion Monomers

The copolymers of the invention include a zwitterion group such as, but not limited to, phosphorylcholine (PC) monomer, Phosphorylcholine is a zwitterion that is analogous to the phospholipid molecules that form cell membranes in living organisms. Consequently, this molecule can be included in the copolymer of the invention for its biocompatibility. The zwitterion monomer also provides water absorption, which is useful for tuning the copolymers for desired drug permeability. In an embodiment, the zwitterion copolymer includes at least about 1.0 mol % to about 50 mol % of a zwitterion monomer.

Examples of suitable zwitterions include phosphorylcholine (which is also known as phosphatidyl choline and phosphocholine), phosphoryl ethanolamine, phosphatidyl ethanolamine, phosphoethanolamine, phosphatidyl serine, and sulfobetaine.

In one embodiment, the zwitterionic monomer includes a zwitterion group with the following general formula.

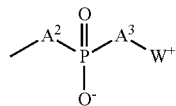

In the foregoing formula, the moieties $A^2$ and $A^3$, which are the same or different, are —O—, —S—, —NH— or a valence bond, and $W^+$ is a group comprising an ammonium, phosphonium or sulphonium cationic group and a group linking the anionic and cationic moieties which in one embodiment is a $C_{1-12}$-alkanediyl group. In another embodiment, the $W^+$ is a $(CH_2)_2{}^+N(R^2)_3$, where $R^2$ are the same or different and each is hydrogen or $C_{1-4}$ alkyl, and m is from 1 to 4.

Alternatively, the zwitterionic group may be a betaine group (i.e., in which the cation is closer to the backbone), for instance a sulpho-, carboxy- or phosphor-betaine. In an embodiment, the betaine group has the formula -$A^4$-$R^3$—$N^+$ $(R^4)_2$—$R^5$—$V^-$, in which $A^4$ is a valence bond, —O—, —S—, or —NH—; V is a carboxylate, sulphonate or phosphate diester (monovalently charged) anion; $R^3$ is a valence bond (together with $A^4$) or alkanediyl, —C(O)alkylene- or —C(O)NH alkylene; the groups $R^4$ are the same or different and each is hydrogen or alkyl of 1 to 4 carbon atoms or the groups $R^4$ together with the nitrogen to which the are attached form a heterocyclic ring of 5 to 7 atoms; and $R^5$ is an alkyanediyl of 1 to 20 carbon atoms, of 1 to 10 carbon atoms, or of 1 to 6 carbon atoms.

In yet another alternative embodiment, the zwitterionic group can be an amino acid moiety in which the alpha carbon atom (to which an amine group and the carboxylic acid group are attached) is joined through a linker group to the backbone of the copolymer. Such groups can be represented by the following general formula.

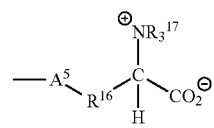

In the foregoing formula, $A^5$ is a valence bond. —O—, —S—, or —NH—; $R^{16}$ is a valence bond (optionally together with $A^5$) or alkanediyl, —C(O)alkylene- or —C(O)NH alkylene; the groups $R^{17}$ are the same or different and each is hydrogen or alkyl of 1 to 4 carbon atoms or the groups $R^4$ together with the nitrogen to which the are attached form a heterocyclic ring of 5 to 7 atoms; and $R^5$ is an alkyanediyl of 1 to 20 carbon atoms, of 1 to 10 carbon atoms, or of 1 to 6 carbon atoms.

In yet another embodiment, the zwitterion-including monomer has the general formula YBX, wherein B is a straight or branched alkylene (alkanediyl), alkyleneoxaalkylene or alkylene oligo-oxaalkylene chain optionally including one or more fluorine atoms up to and including perfluorinated chains or, if X or Y include a terminal carbon atom bonded to B, a valence bond; X is a zwitterionic group; and Y is an ethylenically unsaturated polymerizable group.

2. Dihydroxyphenyl Monomers

The dihydroxyphenyl monomers of the embodiment invention include a dihydroxyphenyl moiety to enhance the adhesion of the polymeric coating to a medical device. The dihydroxyphenyl moiety can be an ortho-dihydroxy catechol group, also referred to as 3,4-dihydroxyphenyl, or a 2,3- dihydroxyphenyl group. The chemical structure of a monomer that includes a 3,4-dihydroxyphenyl moiety is shown below.

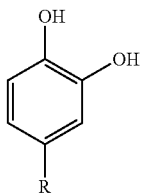

Dihydroxyphenyl moieties have good adhesion to metal hydroxides and other substrates. Mussel adhesion proteins, which are known to bind to a large variety of substrates in an aqueous environment, include large percentages of dihydroxyphenyl moieties, primarily 3,4-dihydroxyphenyl-L-alanine (DOPA). Studies have shown that the adhesion that mussel proteins have for rocks, wood, and metal is due in large part to the modified amino acid DOPA.[1] The dihydroxyphenyl moiety of DOPA bonds tenaciously to inorganic, metal, and metal oxide surfaces. By incorporating a dihydroxyphenyl moiety into the copolymers of the invention, the copolymers of the invention can have enhanced bonding to various surfaces and substrates. In particular, enhanced bonding can be achieved for the surfaces of stainless steel, titania, and nitinol (a superelastic nickel-titanium alloy) based medical devices.

[1] 2. Lee B. P., et al. Biomacromolecules 2002, 3, 1038-1047.

Improved bonding can also be achieved between the copolymers of the invention and living tissue. DOPA has been shown to have an adhesive interaction with polysaccharides and mucin.[2] Since mucin is a component of all mucous membranes, the copolymers of the invention can have an improved affinity for the lining of the arterial wall. This adhesion can assist in maintaining the implantable device in the desired location within the patient's body.

[2] 4. Kui H., et al. Biomacromolecules 2002, 3, 397-406.

The dihydroxyphenyl monomer also includes a polymerizable group. The polymerizable group is selected to be suitable for copolymerization with the zwitterionic monomer. Examples of suitable polymerizable groups include methacryl, acryl, styryl, acrylamido, methacrylamido, sulfovinyl, amido, ester, ethyl, propyl groups, combinations of these, and the like.

The polymerizable group and the dihydroxyphenyl moiety can be separated by a spacer group. The spacer group can be a hydrocarbon chain, cycloaliphatic group, ester group, amide group, thiol, sulfone, carbonate, saccharide, PEG, or combination of these or the like. The spacer group allows for proper spacing of the dihydroxyphenyl moiety from the copolymer carbon backbone chain to facilitate binding between the dihydroxyphenyl moiety and the surface of a substrate.

In one embodiment, the dihydroxyphenyl monomer can be included in the copolymers of the invention in a range from about 1.0 mol % to about 50 mol %.

2. Optional Monomers

Additional monomers can optionally be included in the copolymers of the invention to impart desired properties. In one embodiment, the zwitterion copolymer includes a cationic amine monomer. The cationic amine monomer has a cationic amine side group to further enhance the adhesion of the copolymer to metal surfaces, which are typically anionic. Examples of a suitable cationic amino monomers include N,N'-diethylaminoethyl methacrylate, 2-(dimethylamino) ethyl methacrylate, 2-aminoethyl methacrylate, N-(3-aminopropyl)methacrylamide, 2-(dimethylamino)ethyl styrene, 2-(dimethylamino)ethyl acrylate, N-(2-(N,N'-dimethylamino)ethyl)methacrylamide, N-(3-(N,N'-dimethylamino) propyl)acrylamide, and N-(3-N,N'-dimethylamino)propyl methacrylamide.

The copolymers of the invention may include the cationic amine monomer in an amount in a range from about 0.0 mol % to about 25 mol %. The cationic amine monomer can be included alone or in combination with a hydrocarbon monomer and/or a hydrophilic monomer.

Another additional monomer that can be included in embodiments of the copolymers of the invention is a hydrocarbon monomer. The hydrocarbon monomer includes a hydrocarbon side group to provide non-specific adhesion and/or to modify polymer properties including water swelling and mechanical strength. The hydrocarbon group can be a straight chain, branched, unsaturated or cyclic hydrocarbon of one to sixteen carbon atoms. Examples of suitable hydrocarbon side groups include alkyl, alkenyl, aryl, arylalkyl, alkylaryl, arylkenyl or alkenylaryl sidegroups.

Examples of suitable hydrocarbon monomers include ethyl methacrylate, n-butyl methacrylate, lauryl-methacrylate, methyl methacrylate, isopropyl methacrylate, n-propyl methacrylate, isobutyl methacrylate, sec-butyl methacrylate, tert-butyl methacrylate, n-hexyl methacrylate, cyclohexyl methacrylate, 2-ethylhexyl methacrylate, phenyl methacrylate, benzyl methacrylate, isobornyl methacrylate, trimethylcyclohexyl methacrylate, n-dodecyl methacrylate, methacrylates with pendant groups comprising up to 16 carbons, methyl acrylate, ethyl acrylate, propyl acrylate, n-butyl acrylate, isobutyl acrylate, sec-butyl acrylate, n-hexyl acrylate, cyclohexyl acrylate, phenyl acrylate, benzyl acrylate, styrene, alkyl substituted styrene, ethylene, propylene, 1-butene, and isobutylene.

In an embodiment, the amount of hydrocarbon monomer in the copolymers can be in a range from about 0.0 mol % to about 98 mol %. The hydrocarbon monomer can be included alone or in combination with a cationic amine monomer and/or a hydrophilic monomer.

The optional hydrophilic monomer includes a hydrophilic side group to further modify the polymer's properties. For example, the hydrophilic monomer can be included to increase water swelling and thus drug permeability. Examples of suitable hydrophilic monomers include hydroxyethyl methacrylate (HEMA), hydroxy propyl methacrylate (HPMA), acrylamide, methacrylamide, hydroxyalkyl methacrylamides, 2-hydroxyethyl methacrylate, 3-hydroxypropyl methacrylate, 2-hydroxypropyl methacrylate, hydroxybutyl methacrylate, acrylic acid, methacrylic acid, 2-methoxyethyl acrylate, 2-methoxyethyl methacrylate, 2-ethoxyethyl methacrylate, PEG-methacrylate, PEG-acrylate, polypropylene glycol acrylate, polypropylene glycol methacrylate, vinyl pyrrolidone, allyl alcohol, vinyl sulfonic acid, 2-sulfoethyl methacrylate, 3-sulfopropyl methacrylate, and styrene sulfonic acid.

In one embodiment, the amount of hydrophilic monomer in the copolymers of the invention is in a range from about 0.0 mol % to about 40 mol %. The hydrophilic monomer can be included alone or in combination with a cationic amine monomer and/or a hydrocarbon monomer.

3. Embodiment of Chemical Formula

In one embodiment, the copolymer of the invention has the following chemical formula,

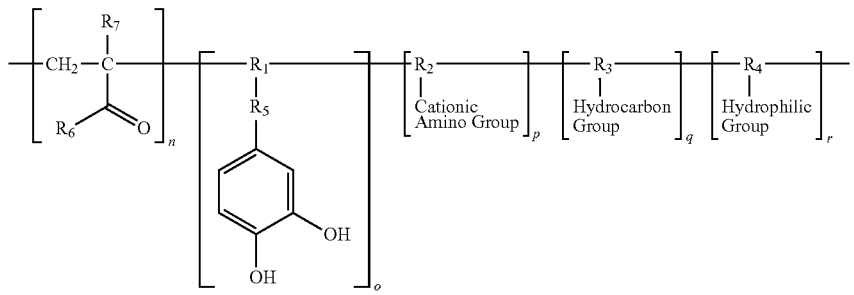

In the foregoing formula, $R_1$-$R_4$ are independently a methacryl, acryl, styryl, acrylamido, methacrylamido, sulfovinyl, amido, ester, ethyl, or propyl; $R_5$ is a hydrocarbon chain, cycloaliphatic group, ester group, amide group, thiol, sulfone, carbonate, saccharide, PEG, or combination thereof; $R_6$ includes a zwitterion group, a linker being a chain of 2-12 carbon atoms, and an ester or amide attachment to the methacryl group; $R_7$ is a methyl, ethyl, or hydrogen group; n is in a range from about 0.005 to about 0.5; o is in a range from about 0.005 to 0.4; p is optionally included in a range from 0.005 to 0.25; q is in a range from 0.005 to 0.98; and r is optionally included in a range from 0.005 to 0.4. In one embodiment, n+o+p+q+r=1. Unless otherwise stated, the monomers shown in the chemical formula above and other chemical formulas herein can be in any order within the copolymer molecule and the monomer linkages shown in the chemical formulas only represent that the monomers are part of the same copolymer molecule. Furthermore, unless otherwise stated, the polymeric molecules can include monomers other than those shown in the chemical formulas.

In an alternative embodiment, the polymer has the following chemical formula,

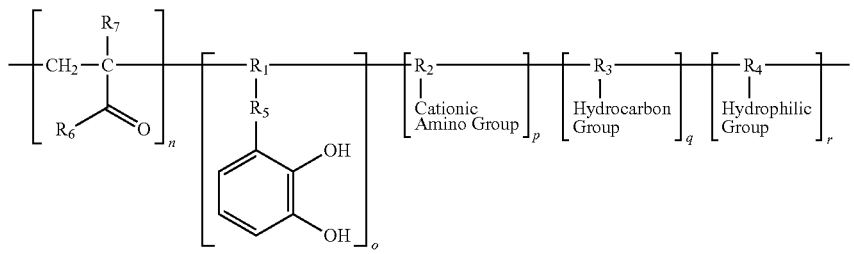

In the foregoing formula, $R_1$-$R_4$ are independently a methacryl, acryl, styryl, acrylamido, methacrylamido, sulfovinyl, amido, ester, ethyl, or propyl; $R_5$ is a hydrocarbon chain, cycloaliphatic group, ester group, amide group, thiol, sulfone, carbonate, saccharide, PEG, or combination thereof; $R_6$ includes a zwitterion group, a linker being a chain of 2-12 carbon atoms, and an ester or amide attachment to the methacryl group; $R_7$ is a methyl, ethyl, or hydrogen group; n is in a range from about 0.005 to about 0.5; o is in a range from about 0.005 to 0.4; p is optionally included in a range from 0.005 to 0.25; q is in a range from 0.005 to 0.98; and r is optionally included in a range from 0.005 to 0.4. In this embodiment, the dihydroxy groups are in the 2,3 position.

In the foregoing formula, the cationic amino group, the hydrocarbon group, and the hydrophilic group can be any suitable cationic, hydrocarbon, or hydrophilic group, respectively, including those listed above.

III. Methods of Manufacturing

The method of manufacturing the copolymers of the invention includes reacting a phosphorylcholine including monomer with a monomer including an ortho-dihydroxyphenyl compound. The copolymers can be synthesized using free radical polymerization, atom transfer radical polymerization, cationic polymerization, anionic polymerization, iniferter polymerization, or other suitable reactions techniques.

Free radical polymerization can be carried out in a solvent using an initiator. Examples of solvents suitable for carrying out the polymerization reaction include alcoholic solvents, such as, but not limited to, methanol, ethanol, and isopropanol. Examples of suitable initiators for carrying out the polymerization reaction include peroxides, such as, but not limited to, benzoyl peroxide, and azo compounds. A specific example of a suitable initiator is 2,2'-azo-bis(2-methylpropionitrile). Those skilled in the art are familiar with the conditions for carrying out the foregoing polymerization reactions and other similar polymerization reactions suitable for yielding the copolymers of the invention.

In one embodiment, the copolymer compositions are manufactured to have a desired $T_g$, when hydrated. The $T_g$ of the copolymer can be calculated by knowing the amount of water absorbed and the $T_g$ derived from measurements of the homopolymer of the respective monomers. In an embodiment, the $T_g$ is calculated using the Fox equation, which is shown below.

$$\frac{1}{T_g^{polymer}} = \frac{W^{pc}}{T_g^{pc}} + \frac{W^{water}}{T_g^{water}} + \frac{W^{Methacrylate}}{T_g^{Methacrylate}}$$

where:
$T_g$=Glass transition temperature of the homopolymer or pure material.
$T_g^{water}$=-40° C.
W=Weight fraction of the components.

Once the water absorption of the polymer is known, which is usually measured experimentally, the copolymer $T_g$ can be estimated with the desired target. In one embodiment the desired target $T_g$ is in a range from about −30° C. to about 37° C. when in the fully hydrated state. In another range, the $T_g$ is between about 0° C. and about 37° C. when hydrated. With a $T_g$ of less than 37° C., the copolymers will have a high degree of polymer mobility when placed in vivo. This feature allows the surface of the polymer to enrich in zwitterionic monomer content, which is advantageous for biocompatibility.

In an alternative embodiment, the copolymer is designed to have a desired $T_g$ for the polymer in the dry state. In an embodiment, the $T_g$ of the polymer when dry is in a range from about −30° C. to about 100° C. or in a range from about 0° C. to about 70° C.

The polymerization reaction can be controlled to produce the copolymers with a desired molecular weight. In one embodiment, the number average molecular weight of the copolymer is in the range from about 20K to about 800K and in another range from about 100K to about 600K.

In an alternative embodiment, the number average molecular weight of the polymer is selected to provide adhesion. In this embodiment, the molecular weight can be in a range from about 2K to about 200K. The adhesive polymer can be used on medical devices that benefit from an adhesive polymer coating.

The copolymers of embodiments of the invention can be manufactured substantially free of cross-linking Copolymers manufactured according to the invention have sufficient mechanical strength when hydrated that cross-linking is not necessary for making a polymer coating suitable for coating an implantable device. The absence of cross-linking can give the copolymers improved elasticity, particularly when dry, which reduces the likelihood of cracking during assembly and use.

The 3,4-dihydroxyphenyl substituted monomers can be made by reacting a polymerizable group with an ortho-dihydroxyphenyl compound. These reactions are typically carried out using known reaction conditions. An example of a suitable reaction for forming a 3,4-dihydroxyphenyl substituted monomer is shown below.

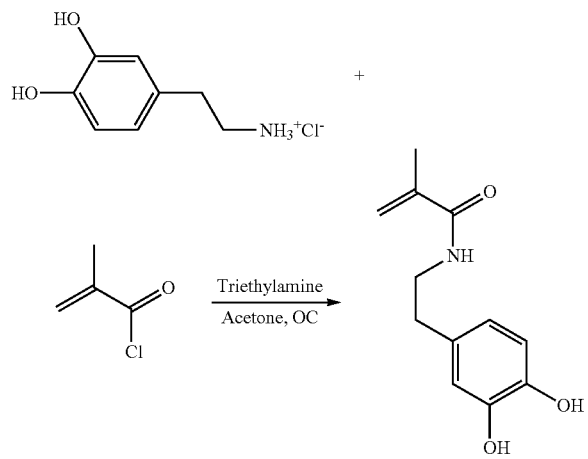

In the forgoing reaction, dopamine hydrochloride is reacted with methacryloyl chloride to yield 2-(3,4-dihydroxyphenyl)-ethyl methacrylamide. Dopamine hydrochloride and methacryloyl chloride are commercially available compounds (e.g., from Aldrich).

Alternately, the dihydroxyphenyl group can be coupled to the polymer backbone after the polymerization is performed. In one such example, the polymerization is done with methacrylic acid instead of the 2-(3,4-dihydroxyphenyl)-ethyl methacrylamide. After the polymer is isolated, dopamine is coupled to the pendant carboxylic acid groups with, for example, dicyclohexylcarbodiimide.

IV. Use of Coatings on Implantable Devices

The foregoing copolymers are suitable for use on any medical device that is compatible with polymer coatings. The copolymers can be used alone as a coating or can be combined with other polymers or agents to form a polymer coating. For example, the polymers may be blended with poly(vinyl pyrrolidinone), poly(n-butyl methacrylate), poly(n-butyl methacrylate) copolymers, methacrylate polymers, acrylate polymers, and/or a terpolymers of hexyl methacrylate, vinyl acetate, and vinyl pyrrolidinone.

The polymer coatings can be applied to a medical device using any techniques known to those skilled in the art or those that may be developed for applying a coating to a medical device. Examples of suitable techniques for applying the coating to the medical device include spraying, dip coating, roll coating, spin coating, powder coating, and direct application by brush or needle. One skilled in the art will appreciate the many different techniques in powder coating. The copolymers can be applied directly to the surface of the implant device, or they can be applied over a primer or other coating material.

In one embodiment, the polymer coating is applied to a medical device using a solvent-based technique. The polymer can be dissolved in the solvent to form a solution, which can be more easily applied to the medical device using one or more of the above mentioned techniques or another technique. Thereafter substantially all or a portion of the solvent can be removed to yield the polymer coating on a surface of the medical device.

Examples of suitable solvents that can be used with the copolymers of the invention include, but are not limited to, dimethylacetamide (DMAC), dimethylformamide (DMF), tetrahydrofuran (THF), dimethylsulfoxide (DMSO), cyclohexanone, xylene, toluene, acetone, n-butanol, i-propanol, methyl ethyl ketone, propylene glycol monomethyl ether, methyl t-butyl ketone, methyl isobutyl ketone, ethyl acetate, n-butyl acetate, ethanol, methanol, chloroform, trichloroethylene, 1,1,1-trichloroethane, methylene chloride, and dioxane. Solvent mixtures can be used as well. Representative examples of the mixtures include, but are not limited to, DMAC and methanol (50:50 w/w); water, i-propanol, and DMAC (10:3:87 w/w); i-propanol and DMAC (80:20, 50:50, or 20:80 w/w); acetone and cyclohexanone (80:20, 50:50, or 20:80 w/w); acetone and xylene (50:50 w/w); and 1,1,2-trichloroethane and chloroform (80:20 w/w).

Examples of suitable implantable devices that can be coated with the copolymers of the invention include coronary stents, peripheral stents, catheters, arterio-venous grafts, bypass grafts, pacemaker and defibrillator leads, anastomotic clips, arterial closure devices, patent foramen ovale closure devices, and drug delivery balloons. The copolymers are particularly suitable for permanently implanted medical devices.

The implantable device can be made of any suitable biocompatible materials, including biostable and bioabsorbable materials. Suitable biocompatible metallic materials include, but are not limited to, stainless steel, tantalum, titanium alloys (including nitinol), and cobalt alloys (including cobalt-chromium-nickel and cobalt-chromium-tungsten alloys). Suitable nonmetallic biocompatible materials include, but are not limited to, polyamides, fluoropolymers, polyolefins (i.e., polypropylene, polyethylene etc.), nonabsorbable polyesters (i.e. polyethylene terephthalate), and bioabsorbable aliphatic polyesters (i.e. homopolymers and copolymers of lactic acid, glycolic acid, lactide, glycolide, para-dioxanone, trimethylene carbonate, ε-caprolactone, and the like, and combinations of these).

The copolymers are particularly advantageous as a coating for stents due to their elongation properties which allows the coated stent to be crimped and expanded without cracking the coating. The stents can be composed of wire structures, flat perforated structures that are subsequently rolled to form tubular structures, or cylindrical structures that are woven, wrapped, drilled, etched or cut.

FIG. 1A shows an example stent 10 coated with a copolymer that includes dihydroxyphenyl moieties. Stent 10 includes a generally tubular body 12 with a lumen. The struts of body 12 (e.g., strut 14) provide a supporting structure for coating the polymers of the invention.

FIG. 1B illustrates a cross-section of the stent of FIG. 1A coated with a polymer coating 16 according to the invention. The polymer coating 16 can be conformal as in FIG. 1B. Alternatively, the coating can be ablumenal, luminal, or any combination thereof. In one embodiment, the copolymers of the invention are elastic at body temperatures and can therefore expand without cracking as the stent expands during use.

The polymer coated stents of the invention can be self-expanding or balloon expandable. The copolymer coatings of the invention can be particularly advantageous for self expanding stents. Self expanding stents are typically restrained by a sheath that is removed during deployment of the stent. The copolymers of the invention can have improved mechanical strength to better withstand the friction exerted on the polymer as the sheath is removed.

In one embodiment, a bioactive agent is associated with the coated medical devices of the invention. The bioactive agent can be associated with a base coat, top coat, mixed with the novel copolymers of the invention, and/or incorporated or otherwise applied to a supporting structure of the medical device.

The bioactive agent can have any therapeutic effect. Examples of suitable therapeutic properties include anti-proliferative, anti-inflammatory, antineoplastic, antiplatelet, anti-coagulant, anti-fibrin, antithrombonic, antimitotic, antibiotic, antiallergic and antioxidant properties.

Examples of suitable bioactive agents include synthetic inorganic and organic compounds, proteins and peptides, polysaccharides and other sugars, lipids, DNA and RNA nucleic acid sequences, antisense oligonucleotides, antibodies, receptor ligands, enzymes, adhesion peptides, blood clot agents, including streptokinase and tissue plasminogen activator, antigens, hormones, growth factors, ribozymes, retroviral vectors, anti-proliferative agents including rapamycin (sirolimus), 40-O-(2-hydroxyethyl)rapamycin (everolimus), 40-O-(3-hydroxypropyl)rapamycin, 40-O-(2-hydroxyethoxy)ethylrapamycin, 40-O-tetrazolylrapamycin (zotarolimus, ABT-578), 40-epi-(N-1-tetrazolyl)-rapamycin, 40-O[2-(2-hydroxy)ethoxy]ethyl-rapamycin, Biolimus A9 (biosensors International, Singapore), deforolimus, AP23572 (Ariad Pharmaceuticals), paclitaxel, docetaxel, methotrexate, azathioprine, vincristine, vinblastine, fluorouracil, doxorubicin hydrochloride, mitomycin, antiplatelet compounds, anticoagulants, antifibrin, antithrombins including sodium heparin, low molecular weight heparins, heparinoids, hirudin, argatroban, forskolin, vapiprost, prostacyclin, prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors including Angiomax ä; calcium channel blockers including nifedipine, colchicine, fibroblast growth factor (FGF) antagonists, fish oil (omega 3-fatty acid), histamine antagonists, lovastatin, monoclonal antibodies, nitroprusside; phosphodiesterase inhibitors, prostaglandin inhibitors, suramin, serotonin blockers, steroids, thioprotease inhibitors, triazolopyrimidine, nitric oxide or nitric oxide donors, super oxide dismutases, super oxide dismutase mimetic, estradiol, anticancer agents, dietary supplements including vitamins, anti-inflammatory agents including aspirin, tacrolimus, dexamethasone, dexamethasone acetate, dexamethasone phosphate, momentasone, cortisone, cortisone acetate, hydrocortisone, prednisone, prednisone acetate, betamethasone, betamethasone acetate, clobetasol, cytostatic substances including angiopeptin, angiotensin converting enzyme inhibitors including captopril, cilazapril or lisinopril, antiallergic agents is permirolast potassium, alpha-interferon, bioactive RGD, and genetically engineered epithelial cells. Other bioactive agents which are currently available or that may be developed in the future for use with DESs may likewise be used and all are within the scope of this invention.

The medical devices of the invention can be used in any vascular, tubular, or non-vascular structure in the body. In an embodiment, a coated stent can be used in, but is not limited to use in, neurological, carotid, coronary, aorta, renal, biliary, ureter, iliac, femoral, and popliteal vessels.

V. Examples

The following are specific examples of copolymers of phosphorylcholine monomers and ortho-dihydroxyphenyl monomers. The following zwitterionic copolymers are useful for coating implantable medical devices.

Example 1

Example 1 describes a copolymer of PC, 2-(3,4 dihydroxylphenyl)ethylmethacrylamide, and n-butyl methacrylate.

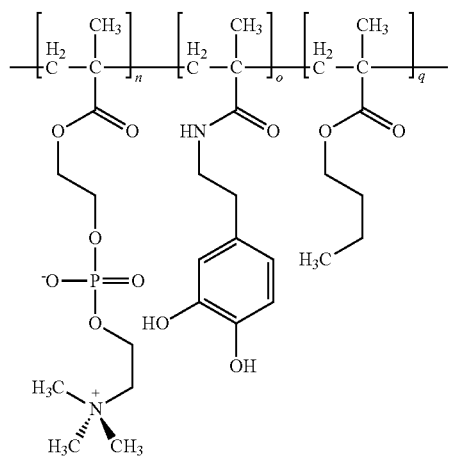

In this copolymer, the n-butyl methacrylate moderates the hydrophilicity of the polymer and enhances the polymers mechanical properties. Percent ranges (mol %) for the monomers are 1%-50% for n, 1%-40% for o, and 10%-98% for q.

Example 2

Example 2 describes a copolymer of PC, 2-(3,4-dihydroxylbenzyl)-methacrylamide, N—N-dimethylaminoethyl methacrylate, and ethyl methacrylate.

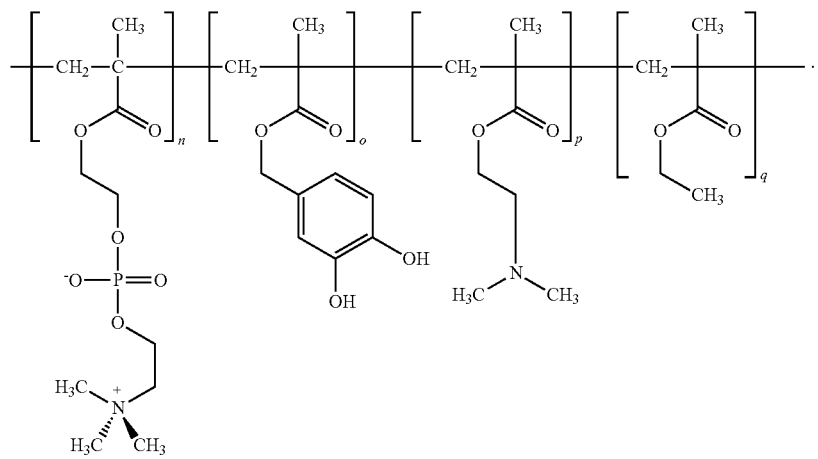

In this copolymer, the dimethylaminoethyl methacrylate enhances the adhesion to anionic surfaces such as, but not limited to, metal oxides. Cationic monomers can enhance the adhesion but their use is typically moderated to avoid potential issues with regard to binding of fibrinogen and platelets. The ethyl methacrylate increases the hardness of the polymer. Percent ranges (mol %) for the monomers are 1%-50% for n, 1%-40% for o, 0.5%-25% for p, and 10%-97.5% for q.

Example 3

Example 3 describes a copolymer of PC, 2-(3,4-dihydroxylphenyl)ethylmethacrylamide, and n-propyl methacrylate.

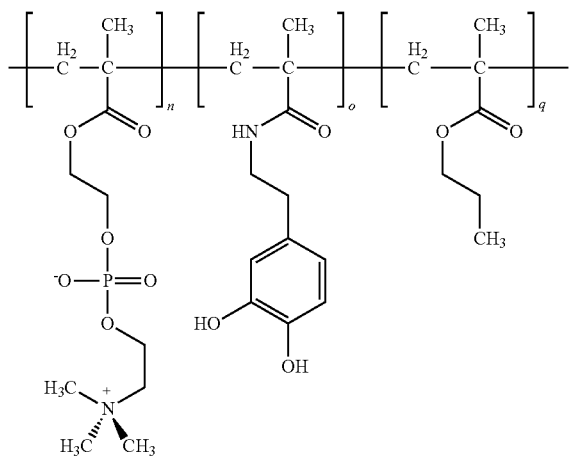

Compared to Example 1, the n-propyl methacrylate has a slightly higher Tg and is a harder monomer than n-butyl methacrylate. Thus, for a given monomer composition, this copolymer will be harder than the copolymer of Example 1. Percent ranges for the monomers are 1%-50% for n, 1%-40% for o, and 10%-98% for q.

Example 4

Example 4 describes a method for manufacturing a drug eluting stent coating using one or more of the polymers of Examples 1-3. In a first step, an optional primer coating is applied to the stent. A primer solution including between about 0.1 mass % and about 15 mass %, (e.g., about 2.0 mass %) of one of the copolymers of Examples 1-3, and the balance, a solvent mixture of ethanol and 1-butanol (having about 50 mass % of ethanol and about 50 mass % of 1-butanol) is prepared. The solution is applied onto a stent to form a primer layer.

To apply the primer layer, a spray apparatus, (e.g., Sono-Tek MicroMist spray nozzle, manufactured by Sono-Tek Corporation of Milton, N.Y.) is used. The spray apparatus is an ultrasonic atomizer with a gas entrainment stream. A syringe pump is used to supply the coating solution to the nozzle. The composition is atomized by ultrasonic energy and applied to the stent surfaces. A useful nozzle to stem distance is about 20 mm to about 40 mm at an ultrasonic power of about one watt to about two watts. During the process of applying the composition, the stent is optionally rotated about its longitudinal axis, at a speed of 100 to about 600 rpm, for example, about 400 rpm. The stent is also linearly moved along the same axis during the application.

The primer solution is applied to a 15 mm Triplex, N stent (available from Abbott Vascular Corporation) in a series of 20-second passes, to deposit, for example, 20 μg of coating per spray pass. Between the spray passes, the stent is allowed to dry for about 10 seconds to about 30 seconds at ambient temperature. Four spray passes can be applied, followed by baking the primer layer at about 80° C. for about 1 hour. As a result, a primer layer can be formed having a solids content of about 80 μg. For purposes of this invention, "Solids" means the amount of the dry residue deposited on the stent after all volatile organic compounds (e.g., the solvent) have been removed. In a manner similar to the application of the primer layer, a polymer-therapeutic solution is prepared and applied using the following formula.

(a) between about 0.1 mass % and about 15 mass %, (e.g., about 2.0 mass % of the copolymer of one or more of Example 1-3;

(b) between about 0.1 mass % and about 2 mass %, for example, about 1.0 mass % of a therapeutic agent. In one embodiment, the therapeutic agent is ABT-578 (available from Abbott Vascular Corp. of Chicago, Ill.); and (c) the balance, a solvent mixture including about 50 mass % of ethanol and about 50 mass % of n-butanol.

The drug-including formulation is applied to the stent in a manner similar to the application of the copolymer primer layer. The process results in the formation of a drug-polymer reservoir layer having a solids content between about 30 μg and 750 μg (e.g., about 225 μg) and a drug content of between about 10 μg and about 250 μg (e.g., about 75 μg).

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

Recitation of ranges of values herein are merely intended to serve as a shorthand method of referring individually to each separate value falling within the range, unless otherwise indicated herein, and each separate value is incorporated into the specification as if it were individually recited herein.

Additional or alternative embodiments include the following:

Embodiment 1

A biocompatible polymer having the formula,

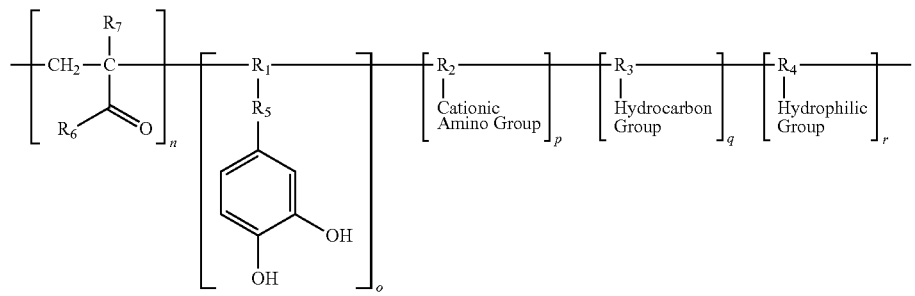

in which, $R_1$-$R_4$ are independently a methacryl, acryl, styryl, acrylamido, methacrylamido, sulfovinyl, amido, ester, ethyl, or propyl;

$R_5$ is a hydrocarbon chain, cycloaliphatic group, ester group, amide group, thiol, sulfone, carbonate, saccharide, PEG, or combination thereof;

$R_6$ includes a zwitterion group, a linker being a chain of 2-12 carbon atoms, and an ester or amide attachment to the methacryl group;

$R_7$ is a methyl, ethyl, or hydrogen group;

n is in a range from about 0.005 to about 0.5;

o is in a range from about 0.005 to about 0.4;

p optionally included in a range from 0.005 to 0.25;

q is in a range from about 0.005 to about 0.98; and r is optionally included in a range from about 0.005 to about 0.4.

Embodiment 2

A biocompatible polymer as in Embodiment 1, wherein n+o+p+q+r=1.

Embodiment 3

A biocompatible polymer as in Embodiment 1, wherein a 3,4-dihydroxyphenyl group is substituted with a 2,3-dihydroxyphenyl group.

Embodiment 4

A biocompatible polymer as in Embodiment 1, in which the zwitterion group is selected from the group consisting of phosphorylcholine, phosphoryl ethanolamine, phosphatidyl ethanolamine, phosphoethanolamine, phosphatidyl serine, sulfobetaine and combinations thereof.

Embodiment 5

A biocompatible polymer as in Embodiment 1, in which the glass transition temperature of the polymer when hydrated is in a range from about −30° C. to about 37° C.

Embodiment 6

A biocompatible polymer as in Embodiment 1, in which the glass transition temperature of the polymer when dry is in a range from about −30° C. to about 100° C.

Embodiment 7

A biocompatible polymer as in Embodiment 1, in which the polymer is substantially free of cross-linking

Embodiment 8

A medical device coating comprising the biocompatible polymer of Embodiment 1.

Embodiment 9

A biocompatible polymer as in Embodiment 1 having the formula,

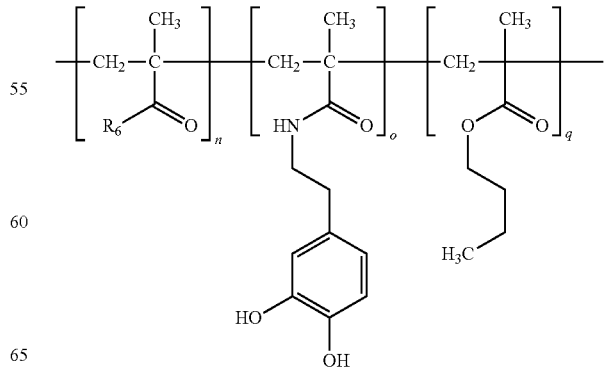

in which, $R_6$ includes a zwitterion group, a linker being a chain of 2-12 carbon atoms, and an ester or amide attachment to the methacryl group;

n is in a range from about 0.01 to about 0.50;
o is in a range from about 0.01 to about 0.4; and
q is in a range from about 0.1 to about 0.98.
n+o+q=1.

Embodiment 10

A biocompatible polymer as in Embodiment 9, in which $R_6$ is selected from the group consisting of phosphorylcholine, phosphoryl ethanolamine, phosphatidyl ethanolamine, phosphoethanolamine, phosphatidyl serine, sulfobetaine and combinations thereof.

Embodiment 11

A medical device coating comprising the biocompatible polymer of Embodiment 9.

Embodiment 12

A biocompatible polymer as in Embodiment 1 having the formula,

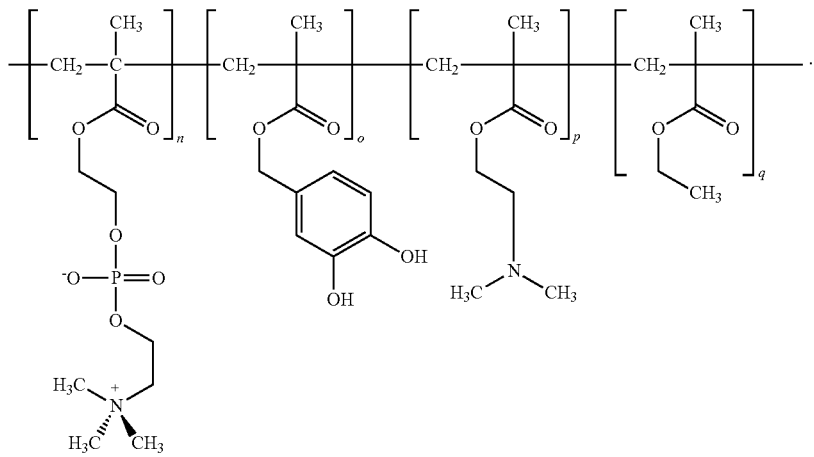

in which, $R_6$ includes a zwitterion group, a linker being a chain of 2-12 carbon atoms, and an ester or amide attachment to the methacryl group;

n is in a range from about 0.005 to about 0.5;
o is in a range from about 0.005 to about 0.4;
p is in a range from about 0.005 to about 0.25;
q is in a range from about 0.1 to about 0.98; and
n+o+p+q=1.

Embodiment 13

A biocompatible polymer as in Embodiment 12, in which $R_6$ is selected from the group consisting of phosphorylcholine, phosphoryl ethanolamine, phosphatidyl ethanolamine, phosphoethanolamine, phosphatidyl serine, sulfobetaine and combinations thereof.

Embodiment 14

A medical device coating comprising the biocompatible polymer of Embodiment 12.

Embodiment 15

A biocompatible polymer as in Embodiment 1 having the formula,

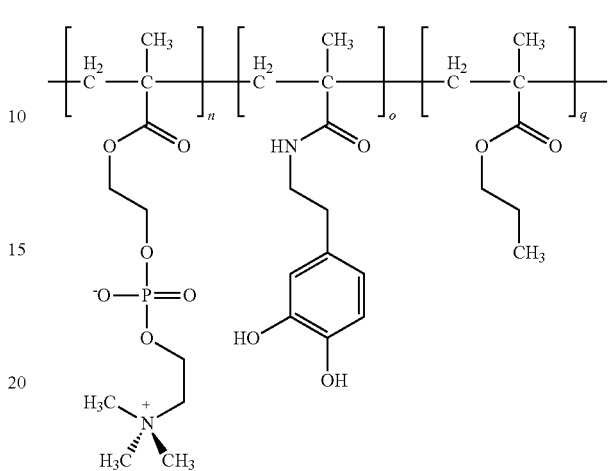

in which, $R_6$ includes a zwitterion group, a linker being a chain of 2-12 carbon atoms, and an ester or amide attachment to the methacryl group;

n is in a range from about 0.005 to about 0.5;
o is in a range from about 0.005 to about 0.4;
q is in a range from about 0.005 to about 0.98; and
n+o+q=1

Embodiment 16

A biocompatible polymer as in Embodiment 14, in which R6 is selected from the group consisting of phosphorylcholine, phosphoryl ethanolamine, phosphatidyl ethanolamine, phosphoethanolamine, phosphatidyl serine, sulfobetaine and combinations thereof.

Embodiment 17

A medical device coating comprising the biocompatible polymer of Embodiment 15.

Embodiment 18

A biocompatible polymer as in Embodiment 1, in which the molecular weight of the polymer is in a range from about 20 kDa to about 800 kDa.

Embodiment 19

A biocompatible polymer as in Embodiment 1, in which the molecular weight of the polymer is in a range from about 2 kDa to about 200 kDa.

Embodiment 20

A biocompatible coating comprising the biocompatible polymer of Embodiment 1 blended with a polymer selected from the group consisting of poly(vinyl pyrrolidinone), poly(n-butyl methacrylate), poly(n-butyl methacrylate) copolymers, methacrylate polymers, acrylate polymers, and/or a terpolymers of hexyl methacrylate, vinyl acetate, and vinyl pyrrolidinone.

Embodiment 21

A medical device comprising a supporting structure having a coating associated therewith, the coating comprising a polymer having the formula,

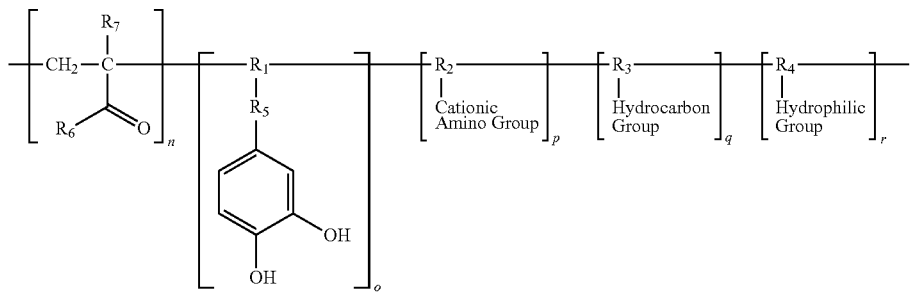

in which, $R_1$-$R_4$ are independently a methacryl, acryl, styryl, acrylamido, methacrylamido, sulfovinyl, amido, ester, ethyl, or propyl;

$R_5$ is a hydrocarbon chain, cycloaliphatic group, ester group, amide group, thiol, sulfone, carbonate, saccharide, PEG, or combination thereof;

$R_6$ includes a zwitterion group, a linker being a chain of 2-12 carbon atoms, and an ester or amide attachment to the methacryl group;

$R_7$ is a methyl, ethyl, or hydrogen group;

n is in a range from about 0.005 to about 0.5;

o is in a range from about 0.005 to about 0.4;

p optionally included in a range from 0.005 to 0.25;

q is in a range from about 0.005 to about 0.98; and r is optionally included in a range from about 0.005 to about 0.4.

Embodiment 22

A medical device as in Embodiment 21, in which n+o+p+q+r=1.

What is claimed is:

1. A medical device comprising a supporting structure having a coating associated therewith, the coating comprising a polymer having the formula

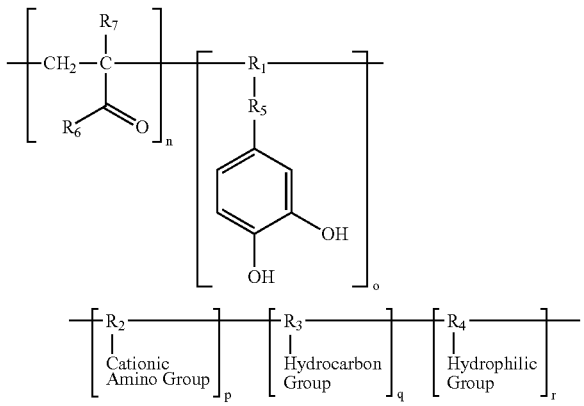

or

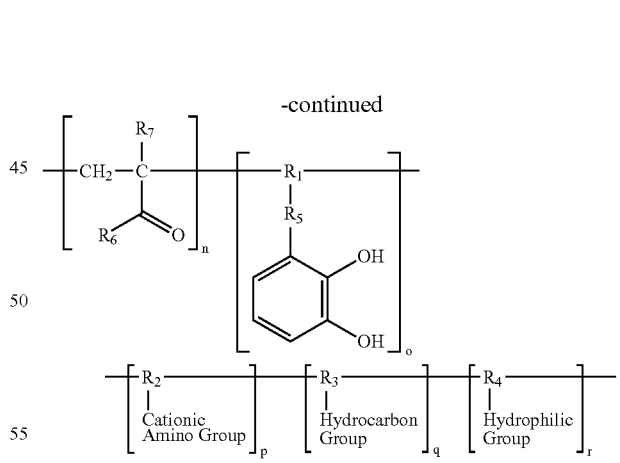

in which, $R_1$-$R_4$ are independently a methacryl, acryl, styryl, acrylamido, methacrylamido, sulfovinyl, amido, ester, ethyl, or propyl;

$R_5$ is a hydrocarbon chain, cycloaliphatic group, ester group, amide group, thiol, sulfone, carbonate, saccharide, PEG, or combination thereof;

$R_6$ includes a zwitterion group, a linker being a chain of 2-12 carbon atoms, and an ester or amide attachment to the methacryl group;

$R_7$ is a methyl, ethyl, or hydrogen group;
n is in a range from about 0.005 to about 0.5;
o is in a range from about 0.005 to about 0.4;
p is in a range from 0 to about 0.25;
q is in a range from 0 to about 0.98; and
r is in a range from 0 to about 0.4;
wherein the zwitterion group has a formula selected from the group consisting of

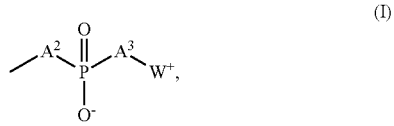

(I)

wherein
the moieties $A^2$ and $A^3$, which are the same or different, are —O—, —S—, —NH— or a valence bond,
$W^+$ is a group comprising an ammonium, phosphonium or sulphonium cationic group and a group linking the anionic and cationic moieties which is a $C_{1-12}$-alkanediyl group;

$-A^4-R^3-N^+(R^4)_2-R^5-V^-$, wherein   (II)

$A^4$ is a valence bond, —O—, —S—, or —NH—;
V is a carboxylate or phosphate diester (monovalently charged) anion;
$R^3$ is a valence bond (together with $A^4$) or alkanediyl, —C(O)alkylene- or —C(O)NH alkylene;
the groups $R^4$ are the same or different and each is hydrogen or alkyl of 1 to 4 carbon atoms or the groups $R^4$ together with the nitrogen to which they are attached form a heterocyclic ring of 5 to 7 atoms; and
$R^5$ is an alkyanediyl of 1 to 20 carbon atoms, of 1 to 10 carbon atoms, or of 1 to 6 carbon atoms;
and

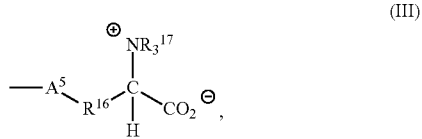

(III)

wherein
$A^5$ is a valence bond. —O—, —S—, or —NH—;
$R^{16}$ is a valence bond (optionally together with $A^5$) or alkanediyl, —C(O)alkylene- or —C(O)NH alkylene;
the groups $R^{17}$ are the same or different and each is hydrogen or alkyl of 1 to 4 carbon atoms or the groups $R^{17}$ together with the nitrogen to which they are attached form a heterocyclic ring of 5 to 7 atoms.

2. The medical device as in claim 1, in which n+o+p+q+r=1.

3. The medical device as in claim 1, in which the cationic amino group is derived from a cationic amino group containing monomer selected from the group consisting of N,N'-diethylaminoethyl methacrylate, 2-(dimethylamino)ethyl methacrylate, 2-aminoethyl methacrylate, N-(3-aminopropyl)methacrylamide, 2-(dimethylamino)ethyl styrene, 2-(dimethylamino)ethyl acrylate, N-(2-(N,N'-dimethylamino)ethyl)methacrylamide, N-(3-(N,N'-dimethylamino)propyl)acrylamide, and N-(3-N,N'-dimethylamino)propyl methacrylamide.

4. The medical device as in claim 1, in which the hydrocarbon group is derived from a hydrocarbon group containing monomer selected from the group consisting of ethyl methacrylate, n-butyl methacrylate, lauryl-methacrylate, methyl methacrylate, isopropyl methacrylate, n-propyl methacrylate, isobutyl methacrylate, sec-butyl methacrylate, tert-butyl methacrylate, n-hexyl methacrylate, cyclohexyl methacrylate, 2-ethylhexyl methacrylate, phenyl methacrylate, benzyl methacrylate, isobornyl methacrylate, trimethylcyclohexyl methacrylate, n-dodecyl methacrylate, methyl acrylate, ethyl acrylate, propyl acrylate, n-butyl acrylate, isobutyl acrylate, sec-butyl acrylate, n-hexyl acrylate, cyclohexyl acrylate, phenyl acrylate, benzyl acrylate, styrene, alkyl substituted styrene, ethylene, propylene, 1-butene, and isobutylene.

5. The medical device as in claim 1, in which the hydrophilic group is derived from a hydrophilic group containing monomer selected from the group consisting of hydroxyethyl methacrylate (HEMA), hydroxy propyl methacrylate (HPMA), acrylamide, methacrylamide, hydroxyalkyl methacrylamides, 2-hydroxyethyl methacrylate, 3-hydroxypropyl methacrylate, 2-hydroxypropyl methacrylate, hydroxybutyl methacrylate, acrylic acid, methacrylic acid, 2-methoxyethyl acrylate, 2-methoxyethyl methacrylate, 2-ethoxyethyl methacrylate, PEG-methacrylate, PEG-acrylate, polypropylene glycol acrylate, polypropylene glycol methacrylate, vinyl pyrrolidone, allyl alcohol, vinyl sulfonic acid, 2-sulfoethyl methacrylate, 3-sulfopropyl methacrylate, and styrene sulfonic acid.

6. The medical device as in claim 1, wherein the zwitterion has formula

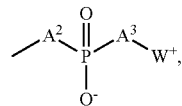

wherein
the moieties $A^2$ and $A^3$, which are the same or different, are —O—, —S—, —NH— or a valence bond,
$W^+$ is a group comprising an ammonium, phosphonium or sulphonium cationic group and a group linking the anionic and cationic moieties which is a $C_{1-12}$-alkanediyl group.

7. The medical device as in claim 6, wherein the $W^+$ is a $(CH_2)_m{}^+N(R^2)_3$, where $R^2$ are the same or different and each is hydrogen or $C_{1-4}$ alkyl, and m is from 1 to 4.

8. The medical device as in claim 1, wherein the zwitterion has formula $-A^4-R^3-N^+(R^4)_2-R^5-V^-$, wherein $A^4$ is a valence bond, —O—, —S—, or —NH—;
V is a carboxylate or phosphate diester (monovalently charged) anion;
$R^3$ is a valence bond (together with $A^4$) or alkanediyl, —C(O)alkylene- or —C(O)NH alkylene;
the groups $R^4$ are the same or different and each is hydrogen or alkyl of 1 to 4 carbon atoms or the groups $R^4$ together with the nitrogen to which they are attached form a heterocyclic ring of 5 to 7 atoms; and
$R^5$ is an alkyanediyl of 1 to 20 carbon atoms, of 1 to 10 carbon atoms, or of 1 to 6 carbon atoms.

9. The medical device as in claim 1, wherein the zwitterion has formula

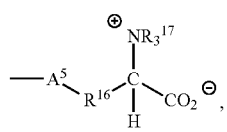

wherein
$A^5$ is a valence bond. —O—, —S—, or —NH—;

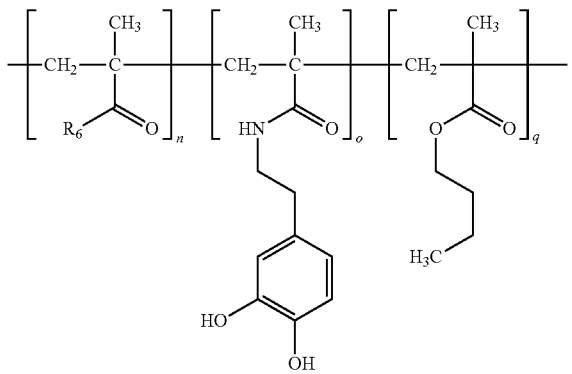

$R^{16}$ is a vlanece bond (optionally together with $A^5$) or alkanediyl, —C(O)alkylene- or —C(O)NH alkylene;

the groups $R^{17}$ are the same or different and each is hydrogen or alkyl of 1 to 4 carbon atoms or the groups $R^{17}$ together with the nitrogen to which they are attached form a heterocyclic ring of 5 to 7 atoms.

10. The medical device as in claim 1, in which the zwitterion group is selected from the group consisting of phosphorylcholine, phosphoryl ethanolamine, phosphatidyl ethanolamine, phosphoethanolamine, phosphatidyl serine, and combinations thereof.

11. The medical device as in claim 1, in which the polymer having the formula,

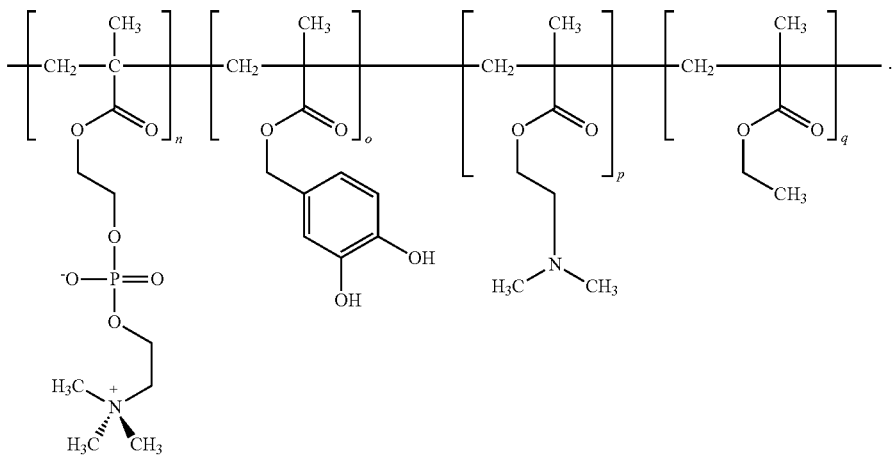

in which,
$R_6$ includes a zwitterion group, a linker being a chain of 2-12 carbon atoms, and an ester or amide attachment to the methacryl group;
n is in a range from about 0.01 to about 0.50;
o is in a range from about 0.01 to about 0.4; and
q is in a range from about 0.1 to about 0.98.
n+o+q=1.

12. The medical device as in claim 11, in which $R_6$ is selected from the group consisting of phosphorylcholine, phosphoryl ethanolamine, phosphatidyl ethanolamine, phosphoethanolamine, phosphatidyl serine, and combinations thereof.

13. The medical device as in claim 1, in which the polymer having the formula, in which,
n is in a range from about 0.005 to about 0.5;
o is in a range from about 0.005 to about 0.4;
p is in a range from about 0.005 to about 0.25;
q is in a range from about 0.1 to about 0.98; and
n+o+p+q=1.

14. The medical device as in claim 1, in which the polymer having the formula,

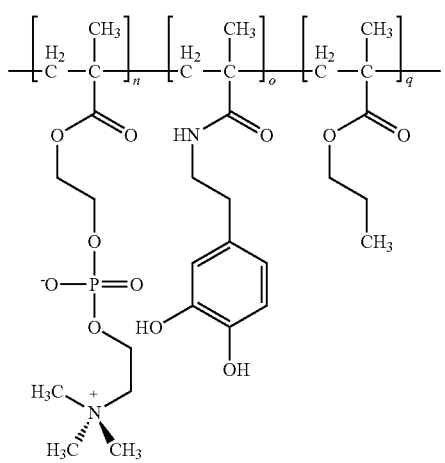

in which,
n is in a range from about 0.005 to about 0.5;
o is in a range from about 0.005 to about 0.4;
q is in a range from about 0.005 to about 0.98; and
n+o+q=1.

15. The medical device as in claim 1, in which the glass transition temperature of the polymer when hydrated is in a range from about −30° C. to about 37° C.

16. The medical device as in claim 1, in which the glass transition temperature of the polymer when dry is in a range from about −30° C. to about 100° C.

17. The medical device as in claim 1, in which the polymer is substantially free of cross-linking.

18. The medical device as in claim 1, in which the molecular weight of the polymer is in a range from about 20 kDa to about 800 kDa.

19. The medical device as in claim 1, in which the molecular weight of the polymer is in a range from about 2 kDa to about 200 kDa.

20. The medical device as in claim 1, in which the biocompatible coating further comprising a polymer selected from the group consisting of poly(vinyl pyrrolidinone), poly(n-butyl methacrylate), poly(n-butyl methacrylate) copolymers, methacrylate polymers, acrylate polymers, and/or terpolymers of hexyl methacrylate, vinyl acetate, and vinyl pyrrolidinone.

21. The medical device as in claim 1, which is an implantable device selected from the group consisting of coronary stents, peripheral stents, catheters, arterio-venous grafts, by-pass grafts, pacemaker, and defibrillator leads, anastomotic clips, arterial closure devices, patent foramen ovale closure devices, and drug delivery balloons.

22. The medical device as in claim 1, which is a stent.

* * * * *